(12) United States Patent
El Glaoui et al.

(10) Patent No.: US 9,233,050 B2
(45) Date of Patent: Jan. 12, 2016

(54) DEVICE AND INSTALLATION FOR JOINING AT LEAST TWO MEDICINE CAPSULES BY ADHESIVE BONDING

(75) Inventors: Mehdi El Glaoui, Geneva (CH); Guillaume El Glaoui, Paris (FR); Jean Hoffelt, La Garenne Colombes (FR); Jean-Pierre Fontaine, Aix les Bains (FR)

(73) Assignee: DUO-GE, Boulogne-Billancourt (FR)

( * ) Notice: Subject to any disclaimer, the term of this patent is extended or adjusted under 35 U.S.C. 154(b) by 434 days.

(21) Appl. No.: 13/811,018

(22) PCT Filed: Jul. 12, 2011

(86) PCT No.: PCT/FR2011/051655
§ 371 (c)(1),
(2), (4) Date: Aug. 30, 2013

(87) PCT Pub. No.: WO2012/017149
PCT Pub. Date: Feb. 9, 2012

(65) Prior Publication Data
US 2014/0008025 A1    Jan. 9, 2014

(30) Foreign Application Priority Data
Jul. 19, 2010 (FR) .................................. 10 55844

(51) Int. Cl.
*B32B 37/10* (2006.01)
*B32B 37/14* (2006.01)
(Continued)

(52) U.S. Cl.
CPC . *A61J 3/07* (2013.01); *A61B 1/041* (2013.01); *A61K 9/4808* (2013.01); *B30B 5/02* (2013.01);
(Continued)

(58) Field of Classification Search
CPC .. B32B 2309/68; B32B 37/1018; B30B 5/02; C09J 5/00; Y10T 156/1744; Y10T 156/1092; A61B 1/041; A61J 3/07; A61K 9/4808
USPC .................. 156/228, 285, 295, 358, 382, 581
See application file for complete search history.

(56) References Cited

U.S. PATENT DOCUMENTS

2005/0191346 A1  9/2005  Nowak et al.
2009/0148514 A1  6/2009  Matthews et al.
(Continued)

FOREIGN PATENT DOCUMENTS

GB   WO 0103676 A1 *   1/2001   ................ A61J 3/07
GB   WO 2009050189 A2 *   4/2009   ........... A61K 9/4808

OTHER PUBLICATIONS

English translation of Written Opinion for PCT/FR2011/051655.*
(Continued)

*Primary Examiner* — Sonya Mazumdar
(74) *Attorney, Agent, or Firm* — B. Aaron Schulman, Esq.; Stites & Harbison, PLLC.

(57) ABSTRACT

The device (1) according to the invention aims to join at least two medicine capsules (A, B) by adhesive bonding in a reliable and economical manner, in particular in the context of industrial production. To do this, this device comprises at least one matrix (10), which at least partially delimits a recess (15), for depositing capsules (Eight, B), and also a chamber (16), this recess and this chamber being separated from each other by a deformable wall (14) of the matrix, which matrix is designed to move elastically, by pneumatic action of its chamber (16), from a first configuration, in which its recess (15) receives the capsules with a glue (Z) interposed between them, to a second configuration, in which its deformable wall (14) at least partially envelops the capsules by flexible deformation, in such a way as to at least partially enclosed these capsules between the deformable wall and a bottom of the recess in order to align them and press them against one another.

16 Claims, 6 Drawing Sheets

(51) Int. Cl.
    *A61J 3/07*     (2006.01)
    *A61K 9/48*     (2006.01)
    *B30B 5/02*     (2006.01)
    *C09J 5/00*     (2006.01)
    *A61B 1/04*     (2006.01)
    *B32B 37/04*    (2006.01)
    *B32B 38/18*    (2006.01)

(52) U.S. Cl.
    CPC ............... *B32B 37/1018* (2013.01); *C09J 5/00* (2013.01); *B32B 2309/68* (2013.01); *Y10T 156/1092* (2015.01); *Y10T 156/1744* (2015.01)

(56) References Cited

U.S. PATENT DOCUMENTS

| | | |
|---|---|---|
| 2011/0027356 A1 | 2/2011 | Lugrin et al. |
| 2011/0160699 A1* | 6/2011 | Imran ................. A61K 31/155 604/514 |
| 2015/0064241 A1* | 3/2015 | Conrad ................ A61B 5/0002 424/451 |

OTHER PUBLICATIONS

International Search Report for PCT/FR2011/051655 dated Nov. 17, 2011.

* cited by examiner

DEVICE AND INSTALLATION FOR JOINING AT LEAST TWO MEDICINE CAPSULES BY ADHESIVE BONDING

The present invention relates to a device and installation for joining at least two medicine capsules by adhesive bonding.

Throughout the present document, the term "capsule" refers to a solid oral galenic form, consisting of a mixture of an active ingredient and excipients, admixtures, vehicles and/or supports. "Solid oral galenic form" refers to a solid oral administration form, i.e. a typical form that may be administered orally as is. This in particular includes caplets, sugar-coated tablets, hard gelatin capsules or flexible-walled globules. This excludes powdered or liquid compositions not included in a solid oral galenic form.

By WO-A-2009/092819, the present applicant proposed to join several medicines in different respective solid galenic forms into a single solid galenic form. One embodiment considered for that joining consists of joining said several medicines by adhesive bonding. Such a galenic form, resulting from the adhesive bonding of several galenic elements, is of substantial interest in light of the issue of the observation of medicinal treatments. These interests are explained in detail in the aforementioned document WO-A-2009/092819, to which the reader may refer for more details.

WO-A-01/03676 proposes making a solid galenic form including two separate compartments, containing respective medicinal powders. To that end, each powder is deposited in a cell of a specific crown, with the insertion of an attached film maintained in the bottom of the cell by a vacuum, then covered with another attached film. By driving the two crowns, the two doses of powder thus filmed are brought closer to each other, until they are pressed against each other with a glue interposed between them.

The aim of the present invention is to propose means for obtaining such an assembly of several galenic elements that are reliable and economical, in particular in the context of industrial production.

To that end, the invention relates to a device for assembling at least two medicine capsules by adhesive bonding, as defined in claim 1.

The idea at the base of the invention is to use a flexible matrix to receive, center and enclose at least two distinct pre-existing capsules, between which glue has been deposited. The flexibility of the matrix according to the invention is such that it can be deformed between two extreme configurations: in one of said two configurations, the matrix generally provides the capsules to be joined with access to a receiving recess that it delimits and it is advantageously configured to impose a predetermined relative positioning between the caplets, to a certain extent by stacking them, whereas, in its other extreme configuration, the matrix is deformed such that a wall of its aforementioned recess better fits the present capsules, until, by complementary shapes, it produces relative pressing thereon with respect to a bottom of the recess, to compress the glue interposed between them and thereby firmly bond them.

In practice, the flexible matrix according to the invention assumes various models and embodiments, as described in detail later. In any case, using such a flexible matrix to manipulate the capsules and accompany their bonding makes it possible to achieve significant production rhythms, typically several thousand items per hour, with effective, reliable material means that comply with the sanitary and security constraints of the pharmaceutical industry. In particular, the action of the matrix to align and enclose the capsules is gentle in that it does not damage said capsules. Furthermore, the matrix according to the invention is easy to wash, in particular dry. Furthermore, within the limits of its elastic deformation capacities, a same matrix can be used to join two or more capsules having different geometries and/or dimensions. In other words, the use of the matrix according to the invention is configurable and therefore economical.

Advantageous features of the assembly device according to the invention, considered alone or according to any technically possible combinations, are specified in dependent claims 2 to 8.

The invention also relates to an installation for assembling at least two medicine capsules by adhesive bonding, as defined in claim 9.

One advantageous embodiment of this installation is specified in claim 10.

The invention will be better understood upon reading the following description, provided solely as an example and done in reference to the drawings, in which.

Figure 1:
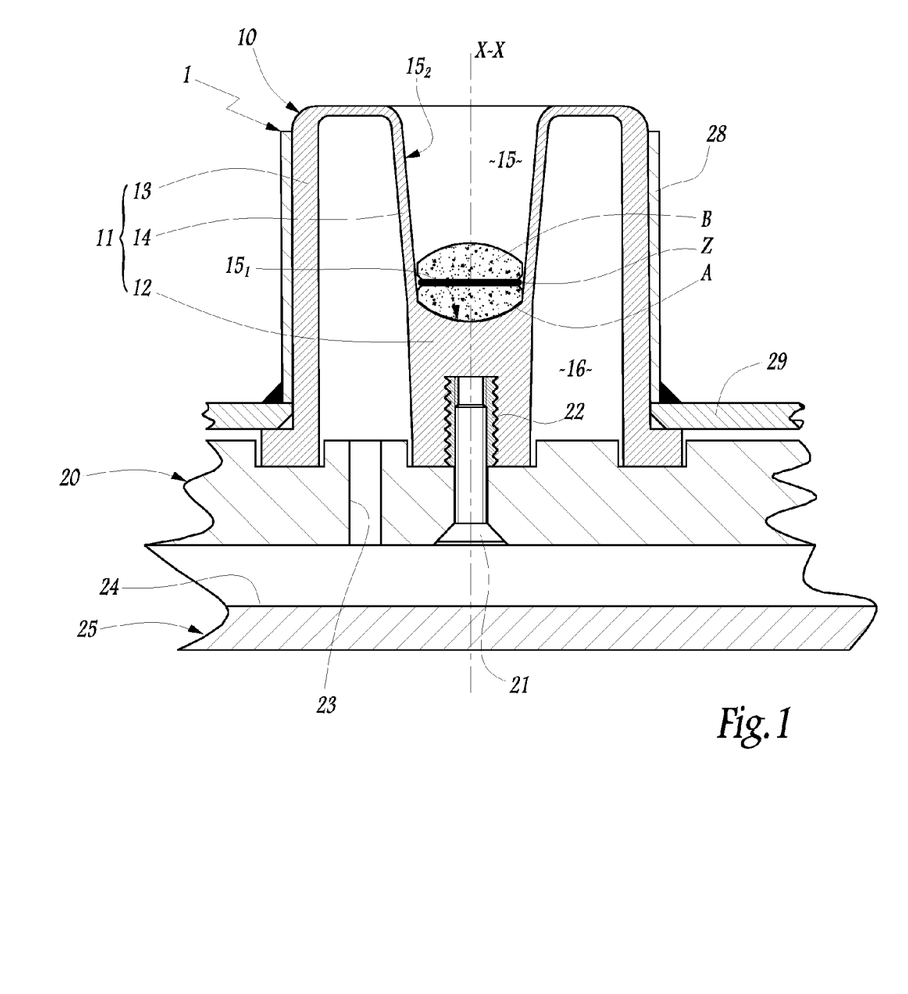
FIG. 1 is a diagrammatic section of a device according to a first embodiment of the invention.

FIG. 1 shows a device 1 making it possible to join at least two medicine capsules A and B by adhesive bonding. In the example shown in the figures, the capsules A and B have substantially identical geometries, i.e., those of a disc having a curved primary surface while the opposite primary surface is at least partially planar to form a planar contact interface between the capsules A and B, with the insertion of a glue Z in the form of a layer. It will be stressed here that the respective geometric forms of the capsules A and B are not limiting on the present invention, i.e., geometries other than those shown in the figures can be considered for these capsules, also having noted that, depending on the case, the capsules A and B may have respective geometries that are different from one another, inasmuch as the selected shapes can establish a contact interface between them where a sufficient quantity of the glue Z is attached to firmly bond the capsules A and B to each other.

As shown in FIG. 1, the device 1 comprises a matrix 10 provided to receive the capsules A and B. More specifically, this matrix 10 comprises or consists of a body 11, which is a single piece in the example considered in the figures and which is made from a flexible material, i.e. a material capable of deforming elastically. In practice, the material making up the body 11 of the matrix 10 is chosen to comply with the sanitary and security constraints of the pharmaceutical industry, in the sense that the material may be put in contact with the medicine capsules A and B without any risk for the health of the consumer who will later use those capsules. In particular, this material is in compliance with the requirements of the Food and Drug Administration. As an example, this material is silicone or silicone-based.

The body 11 of the matrix 10 includes a central base 12, centered on the axis X-X, and here made in the form of a cylinder with a circular base. The body 11 also includes a lateral peripheral wall 13, centered on the axis X-X, here made in a tubular form with a circular base. The central base 12 and the lateral wall 13 are connected to each other by a same transverse wall 14 belonging to the body 11, which extends from the periphery of one of the axial ends of the base 12 to one of the axial ends of the wall 13, running around the entire axis X-X.

In this way, the base 12 and the wall 14 jointly delimit a recess 15 in which the capsules A and B can be deposited, as shown in FIG. 1. Advantageously, the bottom $15_1$ of the recess 15, which is delimited by the axial end of the base 12, is concave, and centered on the axis X-X, so as to force centering of the capsules A and B on the axis X-X through a sliding effect against said bottom $15_1$. Advantageously, said bottom $15_1$ at least partially hugs the capsule. Furthermore, on its side turned toward the recess 15, the wall 14 advantageously has a tapered surface $15_2$, centered on the axis X-X and converging toward the bottom $15_1$ of the recess 15.

At the same time, the base 12, the lateral wall 13 and the wall 14 jointly delimit, on the side of the wall 14 opposite the recess 15, a chamber 16 that runs all around the axis X-X, while surrounding the recess 15. In the example embodiment considered here, this chamber 16 has a substantially annular geometry, centered on the axis X-X.

In practice, making the recess 15 and the chamber 16 inside the matrix 10 is in particular done by appropriate molding of the body, the mold necessary for its molding being simple and economical to manufacture.

Furthermore, the device 1 comprises a fastening support 20 for the matrix 10. In the example embodiment considered here, the support 20 is made in the form of a rigid plate, for example metal or plastic, whereof the surface turned toward the matrix 10 has complementary receiving cavities for the respective axial ends of the base 12 and the lateral wall 13, opposite their axial end connected by the wall 14. A screw 21 is attached through the support plate 20, coaxially to the base 12, until it engages a metal insert 22 embedded in the base 12, as shown in FIG. 1.

The support plate 20 is also passed all the way through by a free passage 23 which at one of its ends emerges in the chamber 16, while its opposite end emerges in a pneumatic distribution duct 24 delimited by a rigid plate 25, for example metal or plastic, on which the support plate 20 is mounted.

Figure 2:
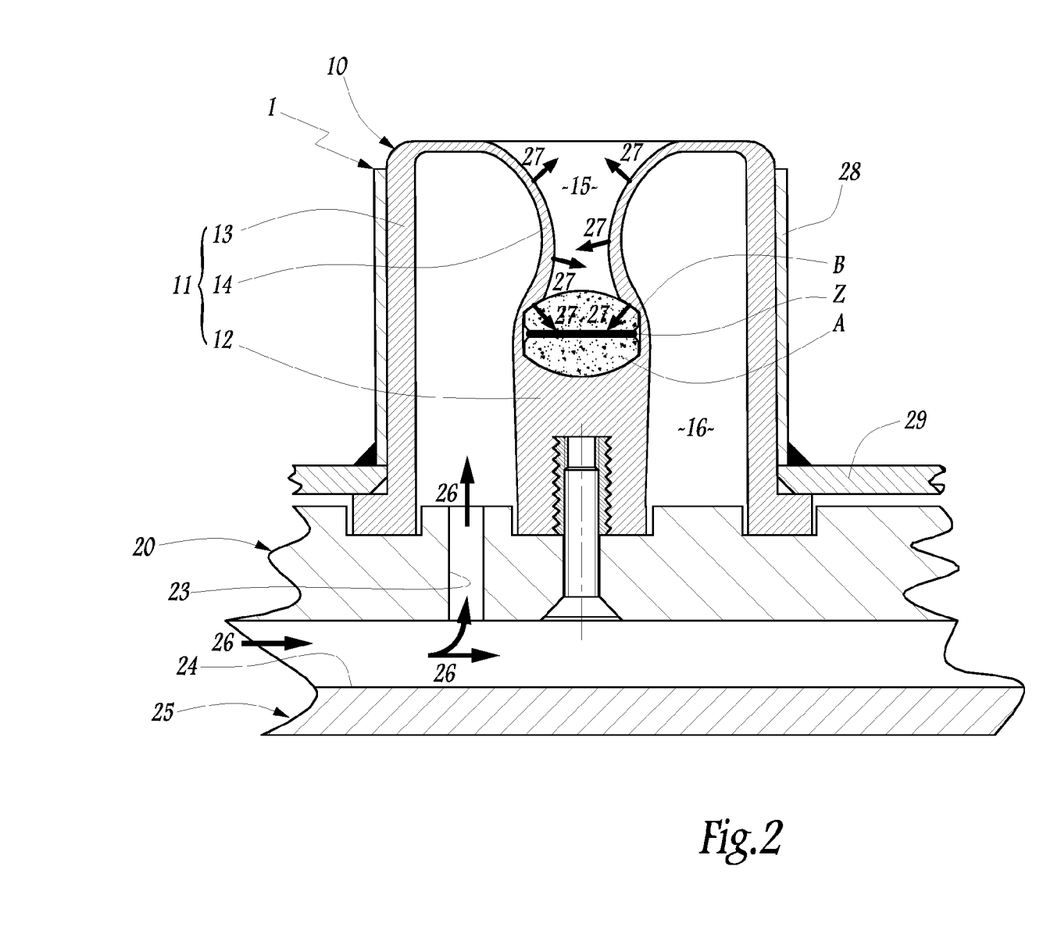
FIG. 2 is a view similar to FIG. 1, illustrating the device in a different service configuration from that of FIG. 1.

During use, the aforementioned duct 24 is connected to a pneumatic source (not shown), preferably a compressed air source. In this way, when the aforementioned source supplies the duct 24 with compressed air, said air circulates through the passage 23, as indicated by the arrows 26 in FIG. 2, to reach the chamber 16, then causing the internal pressure of that chamber to increase. As shown in FIG. 2, under the action of this pneumatic pressure, the chamber 16 inflates, causing the flexible deformation of the matrix 10, more specifically of the wall 14 of its body 11. In other words, the matrix 10 goes from a non-deformed configuration of its body 11, shown in FIG. 1, in which the recess 15 has, opposite its bottom $15_1$, a large enough opening for the capsules A and B to access the inside of the recess, to a deformed configuration of its body 11, shown in FIG. 2, in which the wall 14 is elastically deformed so as, on one side of that wall 14, to allow the inflation expansion of the chamber 16 and, on the opposite side, to allow the constriction of the recess 15, as indicated by the arrows 27 in FIG. 2. In light of the presence of the capsules A and B in the bottom area of the recess 15, in the configuration of FIG. 2, the wall 14 is deformed while at least partially hugging the capsules so as to squeeze them against each other, pressing the glue Z between them. It will be understood that, due to the flexible and gradual deformation of the wall 14 when the matrix 10 goes from its configuration of FIG. 1 to its configuration of FIG. 2, the capsules A and B are gradually enclosed, from top to bottom, between said wall 14 and the bottom $15_1$ of the recess 15, which results in aligning the capsules A and B along the axis X-X, then applying a relative pressure between them while maintaining their aligned arrangement. In practice, to command the gradual deformation of the wall 14 by first accentuating its deformation at the flared end of the recess 15, then propagating that deformation toward the bottom of the recess $15_1$, it is possible to act on a thickness variation of that wall 14.

Commanding the passage of the matrix 10 from its configuration of FIG. 1 to its configuration of FIG. 2 under the action of pneumatic pressure has the additional advantage that, in the event of a puncture of the inflation chamber 16, the body 11 remains in the non-deformed position. Furthermore, using clean and dry compressed air to inflate the chamber 16 is an economical solution inasmuch as compressed air sources are widely available.

In order to concentrate the action of the pneumatic pressure prevailing in the inflated chamber 16 on the wall 14, the device 1 advantageously comprises a stiffener 28 coaxially cinching the lateral wall 13, as shown in FIGS. 1 and 2. In practice, this stiffener 28 is fastened on a plate 29 mounted on the plate of the support 20 and participating in fastening the matrix 10 to said support plate.

Figure 3:
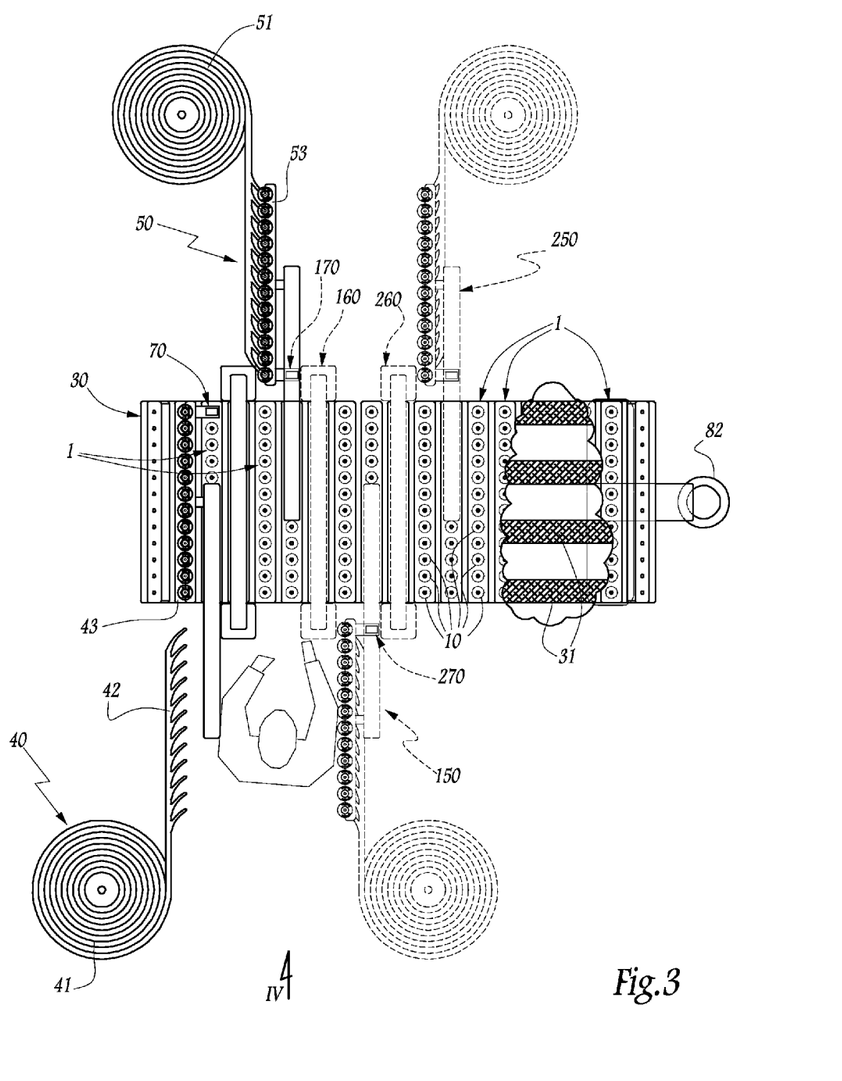
FIG. 3 is a diagrammatic elevation view of an installation according to the invention, including the device of FIG. 1.
Figure 4:
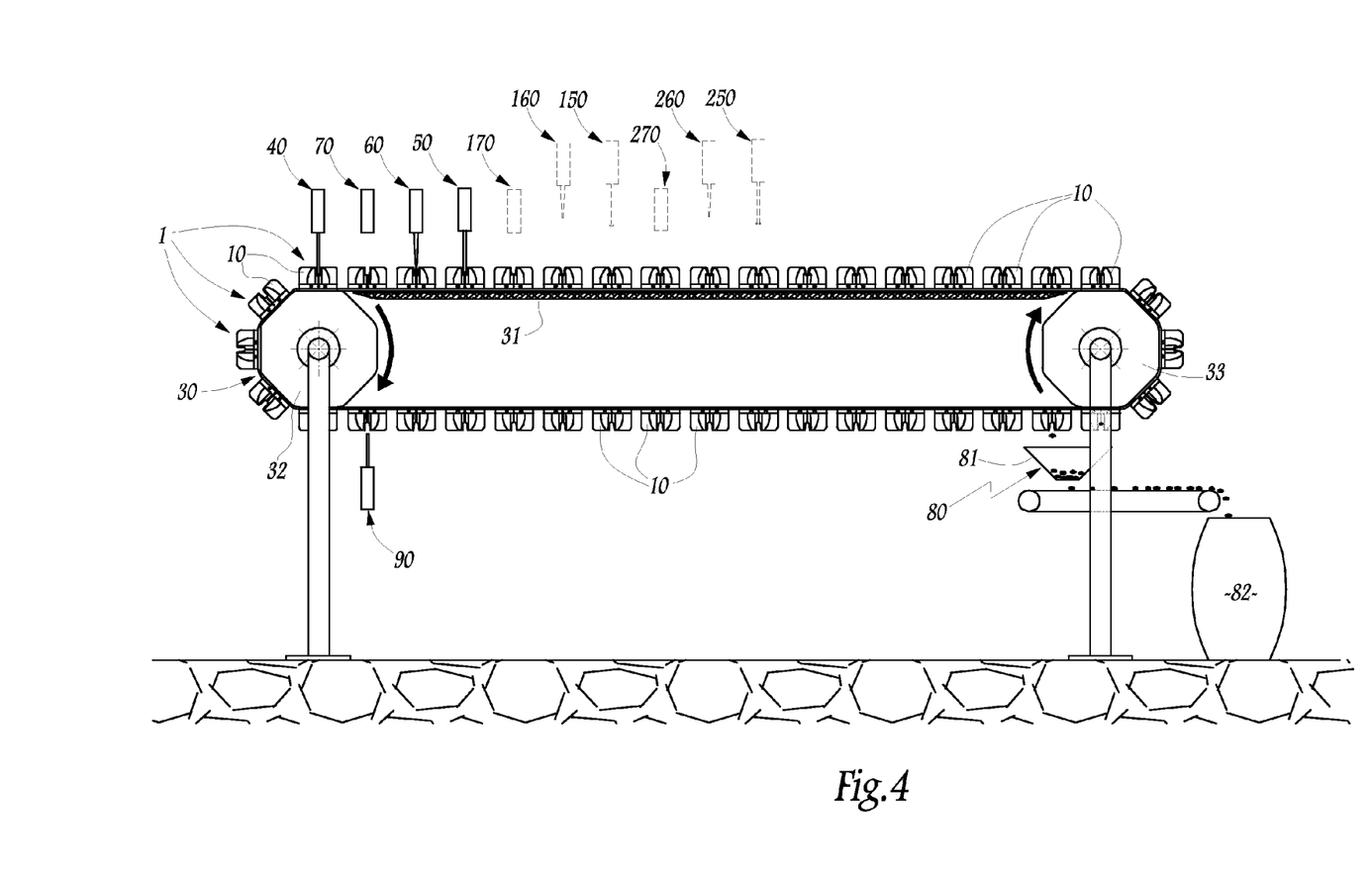
FIG. 4 is a diagrammatic elevation view along arrow IV of FIG. 3.

FIGS. 3 and 4 show an installation comprising several devices 1 mounted on a conveyor 30. More specifically, each device 1 of this installation includes a plurality of matrices 10 described individually in light of FIGS. 1 and 2, said matrices all being supported by the same plate 20, which in turn is mounted on the pneumatic distribution plate 25 whereof the duct 24 jointly supplies as many passages 23 as matrices 10. The matrices 10 of each of said devices 1 are thus distributed behind one another, in the longitudinal direction of the plates 20 and 25, as shown in FIG. 3. As an alternative not shown, rather than providing individual matrices 10 as described above, a single and same matrix may be provided to extend over the entire length of the plates 20 and 25, said single matrix then delimiting, distributed along its longitudinal direction, several recesses 15, each of which is associated with an inflatable chamber 16. In any case, when one observes the device 1 in the direction of the axis X-X as in FIG. 3, said device has a rectilinear series of recesses 15.

The conveyor 30 comprises one or, as shown here, more driving belts 31 of the devices 1, wound around a motor coupling flange 32 and, opposite it, a drum 33 (FIG. 4). By actuating the coupling flange 32, the belts 31 drive the devices 1 distributed along the driving direction of the belts: in this way, when the installation is in use, the matrices 10 of each device 1 are cyclically rotated upward and downward depending on the winding position of the belts 31 around the coupling flange 32 and the drum 33, as shown in FIG. 4.

The installation of FIGS. 3 and 4 also includes several functional stations, distributed around the conveyor 30 and acting on the device 1 situated at the respective level, as outlined below.

Thus, a first station 40 is provided to deposit, in each recess 15 of the device 1 situated at that station, while the matrix or matrices 10 of said device are in their non-deformed configuration of FIG. 1, a medicine capsule A coming from a corresponding reserve of such capsules. Advantageously, this station 40 deposits the capsules A in the device 1 by gravity. In other words, each capsule A falls inside one of the recesses 15, while being guided to the bottom $15_1$ of that recess by the tapered surface $15_2$ of the recess.

In the example embodiment considered in FIGS. 3 and 4, the station 40 comprises a vibrating bowl 41 containing the reserve of capsules A, a ramp 42 for positioning the capsules A, supplied with capsules by the vibrating bowl 41, and a guideway 43 for enclosing the capsules A positioned by the ramp 42. Preferably, the guideway 43 is designed to take the capsules A from the rim 42 using a suction system which, once the guideway 43 is moved to overhang the device 1 situated at the station 40, as shown in FIG. 3, releases the caplets A, which then fall by gravity into the recesses 15 of the matrix or matrices 10 of said device.

The installation of FIGS. 3 and 4 also comprises a station 50 functionally similar to the station 40, but making it possible to deposit a capsule B, rather than a capsule A, in each recess 15 of the matrix or matrices 10 of the device 1 situated outside the station 50. In practice, the station 50 includes the same elements as the station 40, i.e. a vibrating bowl 51, a ramp 52 for positioning capsules B, and an enclosing guideway 53, having noted that, in FIG. 3, unlike the guideway 43 that is shown in its position overhanging one of the devices 1, the guideway 53 is mounted in cooperation with the positioning ramp 52.

Between the stations 40 and 50 along the driving direction of the devices 1 by the conveyor 30, the installation of FIGS. 3 and 4 includes a station 60 applying the glue Z. Preferably, the station 60 includes a system for the gravitational release of drops of glue, in particular by micro-dosing, thereby making it possible to cause a drop of glue Z to fall into each recess 15 of the matrix or matrices 10 of the device 1 situated at the station 60. In practice, in light of the positioning of the station 60 relative to the station 40, the aforementioned drop of glue Z falls on the capsule A that has been deposited beforehand in each of the recesses 15, when the device 1 was at the station 40.

Advantageously and optionally, the installation of FIGS. 3 and 4 also includes a station 70 which, in the driving direction of the devices 1 by the conveyor 30, is situated between the stations 40 and 60 and which makes it possible to detect the presence of a capsule A in each of the recesses 15 of the matrix or matrices 10 of the device 1 situated at that station 70. In the absence of one or more capsules A, the station 70 is designed to notify an operator so as to perform corrective actions, or automatically apply such actions: for example, the station 70 may then come into the downstream station 60 so as to inhibit the application of glue to the concerned device 1.

During use, the conveyor 30 moves the devices 1 successively to the stations 40, 70, 60 and 50, having specified that the matrices 10 of the devices 1 situated at these various stations are in their non-deformed configuration of FIG. 1. Then, after the conveyor 30 moves the device 1 situated at the station 50, control means (not shown in the figures) are actuated to move the matrix or matrices 10 of said device 1 from their non-formed position of FIG. 1 to the deformed position of FIG. 2: the capsules A and B present in said matrix or matrices 10 are enclosed by the body 11 of said matrix or matrices, as explained above in light of FIG. 2. The aforementioned control means thus keep the matrix or matrices 10 of the device 1 in their deformed configuration while the conveyor 30 moves the device 1 until it places the latter overhanging a recovery station 80, the matrix or matrices 10 of said device 1 then being turned downward. The time necessary for the device 1 to be conveyed from the station 50 to the station 80 is thus used to drive the glue Z interposed between the capsules A and B present in the recesses 15 of the device 1. In other words, the sector of the conveyor 30 extending between the stations 50 and 80 corresponds to a driving sector for the glue Z.

At the recovery station 80, the aforementioned control means are deactivated, i.e., by elastic return and/or forced deflation, the body 11 of the or each matrix 10 of the device 1 goes from its deformed configuration of FIG. 2 to its non-deformed configuration of FIG. 1: the capsules A and B bonded to one another then fall into a bell mouth 81 of the recovery station 80, at the outlet of which the bonded capsules are conveyed to a storage container 82.

As one advantageous option, the installation of FIGS. 3 and 4 also includes a washing station 90 (FIG. 4) making it possible to wash, in particular to dry wash, the recesses 15 of the matrix or matrices 10 of the device 1 situated at that station 90. In practice, the wash station 90 is situated, in the driving direction of the devices 1 by the conveyor 30, between the recovery station 80 and the deposition station 40 of the capsule A.

Thus, the devices 1 integrated into the installation of FIGS. 3 and 4 make it possible to join the capsules A and B by adhesive bonding reliably and economically, while allowing high production rhythms.

Figure 5:
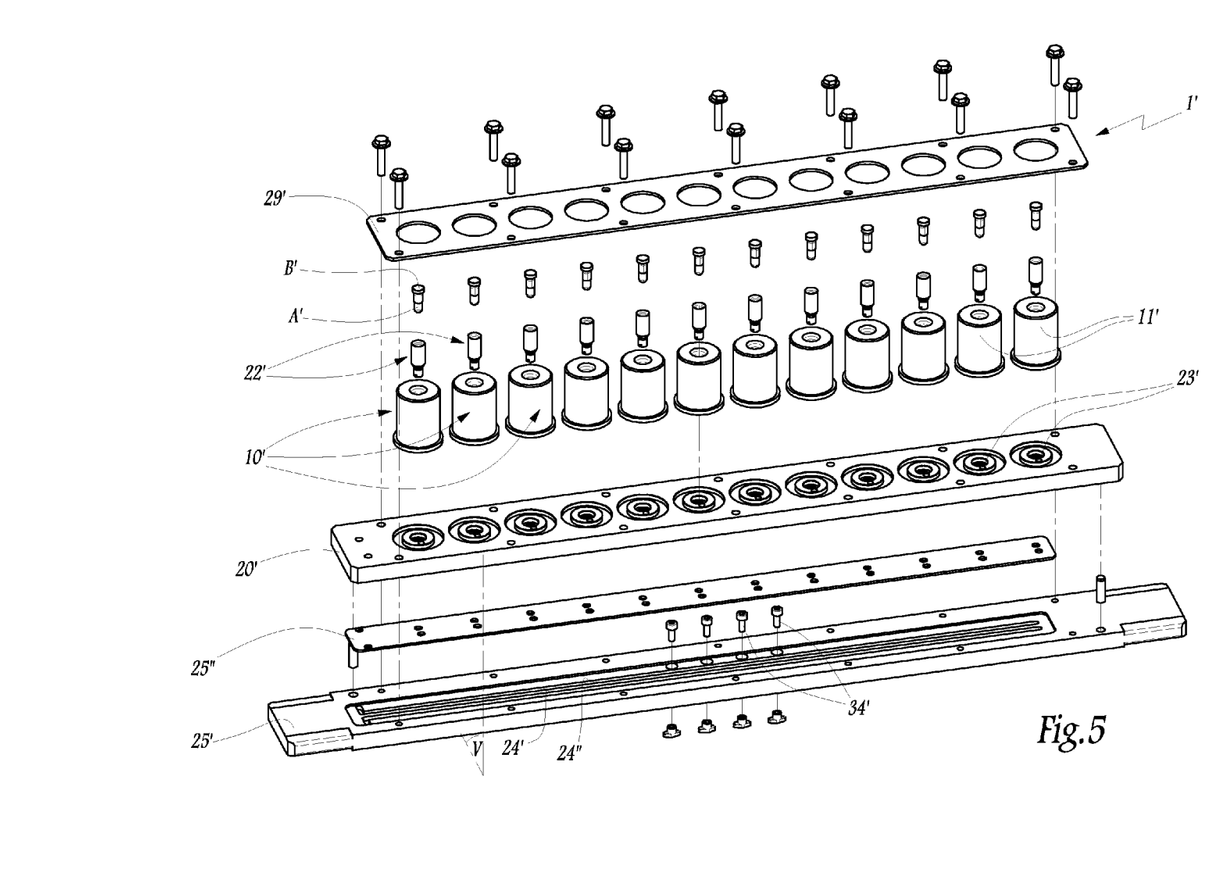
FIG. 5 is an exploded perspective view of a second embodiment of a device according to the invention.
Figure 6:
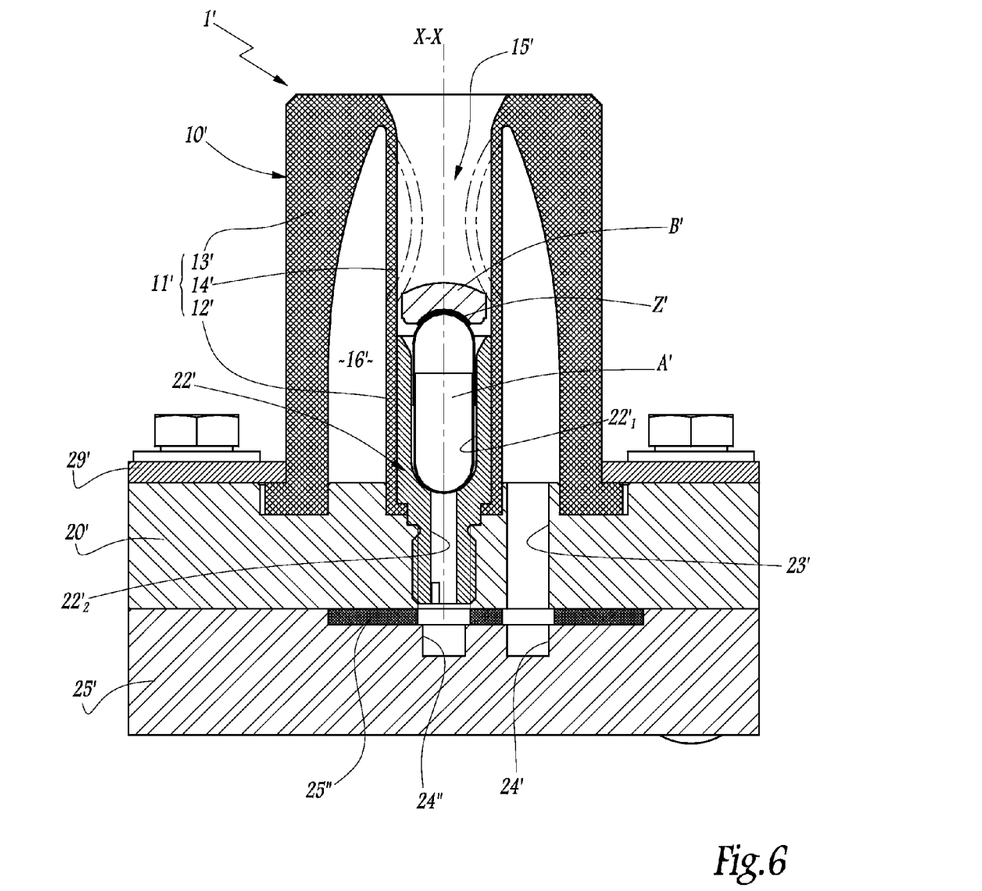
FIG. 6 is a cross-sectional view in plane V of FIG. 5, in the joined state of the device.

FIGS. 5 and 6 show an alternative embodiment of the device 1, referenced 1'. This device 1' may in particular be integrated into the installation of FIGS. 3 and 4, in place of each of the devices 1. Hereafter, we will describe the differences between the devices 1 and 1' in more detail, with the understanding that the components of the device 1' that are functionally similar to the components of the device 1 bear the same references as the latter, followed by '. In this way, the device 1' includes a plurality of matrices 10' supported by a same plate 20', which in turn is mounted on a pneumatic distribution plate 25' and to which a plate 29' is joined for fastening the matrices. Each matrix 10' consists of a flexible body 11' including a central base 12' and a lateral peripheral wall 13', as well as a deformable transverse wall 14' connecting them to each other, all three of which are centered on the axis X-X.

As for the plate 25, the plate 25' is designed to be fastened on the conveyor 30 or a similar conveyor, typically using screws referenced 34' in FIG. 5. Similarly to the device 1, each matrix 10' of the device 1' delimits an inflatable chamber 16' in which a passage 23' emerges passing through the support plate 20'. This passage 23' thus connects the chamber 16' to a pneumatic distribution duct 24' delimited in the plate 25'.

Unlike the device 1, the fastening of each matrix 10' to the support plate 20' is partially done by a rigid insert 22' that is screwed into the support plate 20' from the surface thereof turned toward the matrix 10'. To that end, the base 12' of each matrix 10' has, over its entire axial dimension, a tubular shape centered on the axis X-X and open at both ends thereof. At its end turned toward the support plate 20', the tubular base 12' emerges on a tapping for receiving a threaded portion of the insert 22', provided in the plate 20'. Thus, subject to the insertion, along the axis X-X, of the insert 22' successively inside the wall 14' and the base 12', said insert is attached and screwed to the support plate 20', while occupying the inner volume of the base 12'. In this way, the sensor 22' forms a bottom wall for the recess 15 for depositing capsules N and B' to be adhesively bonded, inwardly delimited by the wall 14'.

A first interest of this arrangement lies in the fact that the insert 22' stiffens the base 12', thereby keeping the latter in place.

A second interest is related to the fact that this insert 22' is advantageously configured to receive and shim the capsule N first deposited in the matrix 10', by at least partially hugging the capsule A'. Thus, in the example embodiment considered in FIGS. 5 and 6, each insert 22 delimits an elongated cavity $22'_1$, centered on the axis X-X and emerging in the recess 15', so as to receive the majority of the capsule A', which here corresponds to a hard gelatin capsule, in a complementary manner.

During use, the device 1' is used in the same way as the device 1. In particular, when the chamber 16' of each matrix 10' is inflated by the compressed air supplied by the duct 24', the wall 14' goes from its non-deformed configuration, shown in solid lines in FIG. 6, to a deformed configuration, shown in mixed lines in FIG. 6 and in which said wall aligns, then presses the capsule B', which here is comparable to a tablet, against the capsule N, while squeezing the glue Z' between said capsules.

A third interest related to the insert 22' concerns the possibility of facilitating the release of the capsules A' and B' after their adhesive bonding. To that end, as shown in FIG. 6, the insert 22' inwardly delimits a through channel $22'_2$, which is centered on the axis X-X and connects its cavity $22'_1$ to a pneumatic distribution duct 24" delimited by the plate 25'. This duct 24" is distinct from the duct 24', while being sealed relative thereto by a flat seal 25" attached between the plates 20' and 25'. In this way, after the capsules N and B' have been adhesively bonded to one another, subject to the supply of compressed air from the duct 24' ensuring inflation of the chamber 16', the supply from the duct 24' is interrupted in favor of the duct 24": pressurized air then circulates through the channel $22'_2$ of the insert 22' of each of the matrices 10', up to the recess 15', to eject the adhesively bonded capsules N and B' by blowing.

Various developments and alternatives to the devices 1 and 1', as well as the installation of FIGS. 3 and 4, can also be considered. For example:
- to facilitate the release of the adhesively bonded capsules A and B with respect to the matrix 10, a blowing channel for the capsules, functionally similar to the channel $22'_2$ described in light of FIG. 6, can be provided through the base 12; at one of its ends, this blowing channel emerges directly in the bottom $15_1$ of the recess 15, while its opposite end is connected, by means of the plates 20 and 25 formed accordingly, to a compressed air circuit distinct from that supplying the chamber 16;
- rather than being commanded by pressure, the transition of the matrix 10 or 10' between its non-deformed and deformed configurations may be obtained by a reduced pressure, i.e. by air suction;
- by acting on the thickness of the lateral wall 13, the stiffener 28 may be eliminated, as is the case for the device 1';
- the recovery station 80 may advantageously integrate means for sorting the adhesively bonded capsules that it handles, so as to separate products presumed to be good and capsules considered to be poorly bonded or non-compliant;
- the shape of the matrix 10 or 10' is not limited to that shown in the figure; likewise, embodiments other than the components 20, 21, 22, 25 and 29 or 20', 22', 25' and 29' can be considered for the assembly and pneumatic command of said matrix;
- the number of capsules that the device 1 or 1' can join to one another by adhesive bonding is not limited to two; on the contrary, three, four, or even more capsules may be adhesively bonded to one another using the device 1, inasmuch as each recess 15 or 15' of the matrix or matrices 10 or 10' is sized accordingly; in that case, the installation of FIGS. 3 and 4 is completed by as many stations as needed, as for example indicated in dotted lines in FIGS. 3 and 4: depending on the direction of movement of the devices 1 by the conveyor 30, we have thus provided, between the stations 50 and 80, on the one hand the series of a detection station 170, a glue application station 160, and a station 150 for depositing a third capsule, which are functionally similar to the stations 70, 60 and 50, then, on the other hand, the series of a detection station 270, a glue application station 260, and a station 250 for depositing a fourth capsule, which are also functionally similar to the stations 70, 60 and 50; and/or
- the arrangement around the devices of the stations 40, 50, 60 and 70, as well as, if applicable, the stations 150, 160, 170, 250, 260 and 270 is not limited to that shown in FIG. 3; for example, for bulk reasons, all of the stations may be arranged on a single and same side of the conveyor 30.

The invention claimed is:

1. A device for joining at least two medicine capsules by adhesive bonding,
wherein the device comprises at least one matrix which at least partially delimits a recess, for depositing capsules and a chamber, this recess and this chamber being separated from each other by a deformable wall of the matrix, which matrix is designed to move elastically, by pneumatic action of its chamber, from a first configuration, in which the recess of the matrix receives the capsules with a glue interposed between them, to a second configuration, in which the deformable wall of the matrix at least partially envelops the capsules by flexible deformation, in such a way as to at least partially enclose these capsules between the deformable wall and a bottom of the recess in order to align them and press them against one another.

2. The device according to claim 1, wherein the matrix is designed to move from its first configuration to its second configuration by the action of pneumatic pressure that inflates the chamber.

3. The device according to claim 2, wherein the recess has a concave bottom for centering the capsules, which is delimited by the matrix, and in that, when the matrix is in its first configuration, the deformable wall has, on the side of the recess, a substantially tapered surface converging toward the bottom of the recess.

4. The device according to, claim 2, wherein the device comprises a rigid insert for receiving and shimming one of the capsules which is arranged in a base of the matrix from which the deformable wall extends, and which forms a bottom for the recess.

5. The device according to claim 2, wherein the deformable wall has a greater capacity for flexible deformation than the rest of the matrix.

6. The device according to claim 2, wherein the device comprises both a support for fastening the matrix, which delimits a passage for inflating the chamber, and a pneumatic distribution plate, on which the fastening support is mounted and which jointly supplies several inflation passages emerging in respective chambers delimited either by an equal number of individual matrices.

7. The device according to claim 1, wherein the matrix is designed to move from its first configuration to its second configuration by the action of a pneumatic vacuum that suctions the air from its chamber.

8. An installation for joining at least two medicine capsules by adhesive bonding, wherein the installation comprises:
at least one joining device according to claim 1,
first means for providing a first of the capsules to be joined to the matrix of the device while that matrix is in its first configuration;
second means for providing a second capsule to be joined to the matrix of the device while that matrix is in its first configuration;

application means for applying a glue on the capsule(s) received by the matrix of the device while that matrix is in its first configuration, driving means for relative driving between the device on the one hand and the first means, the second means and the application means on the other hand, and control means, for moving the matrix between its first and second configurations.

9. The installation according to claim 8, wherein the driving means are designed both to place the matrix accessible from the top for the capsules provided by the first and second means, and for the glue applied by the application means, and to turn the matrix downward, on the one hand, after the control means have moved that matrix from its first configuration to its second configuration and, on the other hand, before the control means move said matrix from its second configuration to its first configuration.

10. The device according to claim 5, wherein, so that the deformable wall has a greater capacity for flexible deformation than the rest of the matrix, the rest of the matrix is cinched by a stiffener.

11. The device according to claim 5, wherein, so that the deformable wall has a greater capacity for flexible deformation than the rest of the matrix, the rest of the matrix has a greater thickness than the deformable wall.

12. The device according to claim 5, wherein the device comprises a rigid insert for receiving and shimming one of the capsules, which is arranged in a base of the matrix, from which the deformable wall extends, and which forms a bottom for the recess, and wherein so that the deformable wall has a greater capacity for flexible deformation than the rest of the matrix, the rest of the matrix is kept in place by the insert.

13. The device according to claim 6, wherein the pneumatic distribution plate also supplies at least one channel for blowing bonded capsules, which emerges in each recess.

14. The device according to claim 2, wherein the device comprises both a support for fastening the matrix, which delimits a passage for inflating the chamber, and a pneumatic distribution plate, on which the fastening support is mounted and which jointly supplies several inflation passages emerging in respective chambers delimited by a shared matrix.

15. The installation according to claim 8, wherein the control means are pneumatic.

16. The device according to claim 14, wherein the pneumatic distribution plate also supplies at least one channel for blowing bonded capsules, which emerges in each recess.

\* \* \* \* \*